United States Patent [19]
Pettit et al.

[11] Patent Number: 4,611,066
[45] Date of Patent: Sep. 9, 1986

[54] BRYOSTATINS 4 TO 8

[75] Inventors: George R. Pettit, Paradise Valley; Cherry L. Herald; Yoskiaki Kamano, both of Tempe, all of Ariz.

[73] Assignee: Arizona State University, Tempe, Ariz.

[21] Appl. No.: 639,898

[22] Filed: Aug. 10, 1984

[51] Int. Cl.$^4$ ............................................ C07D 493/22
[52] U.S. Cl. ...................................................... 549/267
[58] Field of Search ........................................ 549/267

[56] References Cited
PUBLICATIONS

Pettit, G. R., et al., Nature, 1970, 227:962–963.
Villela, G. G., Proc. Soc. Exptl. Biol. Med., 1948, 68:531–553.
Carle', J. S., et al., J. Org. Chem., 1980, 45:1586–1589; 1981, 46:3440–3448.
Okami, Y., et al., J. Antibiot., 1976, 29:1019.
Nakamura, H., et al., J. Antibiot., 1977, 3.0;714.
Copending application Ser. No. 513,148, filed 12 Jul. 1983.

Primary Examiner—Jane T. Fan
Attorney, Agent, or Firm—Lawrence T. Welch

[57] ABSTRACT

New and potent antineoplastic agents designated bryostatin 4, bryostatin 5, bryostatin 6, bryostatin 7, and bryostatin 8 have been isolated from the marine animal *Bugula neritina* L. and *Amatnea convoluta* (*Bryozoan phylum*).

6 Claims, No Drawings

BRYOSTATINS 4 TO 8

Financial assistance was provided by Contract NO1-CM-97262 with the Division of Cancer Treatment, NCI, National Institutes of Health, DHW, Grant Nos. CA164049-01 through 07 awarded by the National Cancer Institute, DHW, Mrs. Mary Dell Pritzlaff, the Olin Foundation (Spencer T. and Ann W.), the Fannie C. Rippel Foundation, Mrs. Eleanor W. Libby, the David Ware Waddell Foundation, Mrs. Pearl Spear, and Mr. Robert B. Dalton. For other very helpful assistance we are pleased to thank Drs. J. D. Douros, J. J. Einck, D. Gust, R. R. Inners, L. W. Knapp, P. Lohavanijaya, M. I. Suffness, J. M. Schmidt, J. Witschel, Jr., Mr. M. A. Carlson, Miss B. L. Norfleet, Miss K. M. Welch, the Smithsonian Institution Oceanographics Sorting Center, and the National Science Foundation Regional Facility at the University of South Carolina (CH78-18723). Support was also provided by NIH CA24487 (JC), and the National Science Foundation.

DESCRIPTION

1. Background of the Invention

The present invention provides novel compositions of matter. In particular, the present invention provides novel, highly active, macrocyclic lactone antitumor antibiotics, bryostatin 4, bryostatin 5, bryostatin 6, bryostatin 7, and brystatin 8, which are isolated from *Bugula neritina* and *Amathia convoluta*, both marine bryozoans.

2. Prior Art

The only prior chemical investigations of bryozoa appear to be (1) our initial report that certain bryozoa such as *Bugula neritina* contain anticancer constituents (Pettit, G. R.; J. F. Day; J. L. Hartwell; H. B. Woods, *Nature*, 1970, 227: 962-963; (2) a preliminary study of an adrenochrome-like pigment in the same species (Villela, G. G. *Proc. Soc. Exptl. Biol. Med.* 1948, 68: 531-553); and (3) isolation of the indoles flustramines A and B from *Flustra foliacea* (Carle', J. S.,; Christopherson, D., *J. Org. Chem.* 1980, 45: 1586-1589; Carle', J. S.; Christopherson, C., *J. Org. Chem.* 1981, 46: 3440-3448). Of the presently known cyclic ionophores, only the *Streptomyces griseus* component aplasmomycin seems distantly related to the bryostatins. (Okami, Y.; Okazaki, T.; Kitahara, T.; Umezawa, H.; *J. Antibiot.* 1976, 29: 1019; and Nakamura, H.; Iitaka, Y.; Kitahaa, T.; Okazaki, T.; Okami, Y., *J. Antibiot.* 1977, 3.0: 714). Bryostatins 1, 2 and 3 are described in copending application Ser. No. 513,148, filed July 12, 1983.

SUMMARY OF THE INVENTION

The present invention particularly provides: a compound of the Formula I,
wherein R is
(a) —COCH$_2$CH$_2$CH$_3$, or
(b) —COCH$_3$; and
wherein R$_1$ is
(a) —COCH$_2$CH(CH$_3$)$_2$,
(b) —COCH$_2$CH$_2$CH$_3$, or
(c) —COCH$_3$,
or an acylate thereof.

These compounds are named herein as Bryostatins 4-8, as shown in Chart C.

DESCRIPTION OF THE ORGANISMS

Marine animals of the phylum Ectoprocta (usually termed Bryozoa or Polyzoa) are colonial filter-feeders and each member (polypide) is enclosed in a separate unit (zooecium). Because of their superficial appearance Bryozoa are commonly know as sea-mats and false corals.

*Bugula neritina* (Linnaeus) is a widely distributed moss-like bryozoan and is well known for its ability to attach to ship hulls. One type of *Bugula neritina* polypide (an avicularium) resembles the beak of a bird and by closing one jaw against the other it is able to protect the colony from univited encroachment. Such avicularia are a common component of *B. neritina*.

*B. neritina* and other marine bryozoans are described by J. H. Day in "A Guide to Marine Life on South African Shores," Balkema, A.A., Cape Town, 1974, p. 123; and by P. H. Benson and R.W. Moncreiff in "The Effects of Zinc and pH on Larval Attachment of the Common Fouling Organism, *Bugula neritina*"; Compt. Rend. du Contres. International de la Corrision Marine et de Salissures. 4th Antibes and Juan-le-Pins, Fr., July 14-18, 1976.

The *Bugula neritina* specimens were collected from Onterrey Bay, Calif. (36° N. latitude, 122° W. longitude). They were collected at low tidal depths of 0–5 ft. Other locations where these organisms have been collected include Toyko Bay, Japan (35° N, 140° E.) and sites near Sinaloa, Mexico and Alligator Harbor, Fla. Extracts of *B. neritina* from three separate collections all contained antineoplastic activity. *Anathia convoluta* occurs in small shrub-like clusters from 1–3 cm. tall where each individual animal of the greyish-brown colony approximates 0.1 mm. in size. See R. Woolcott, et al., Biology of Bryosoans, (Academic Press, N.Y., 1981) and J. S. Rylands, Bryosoan, (Hutchinson and Co., Ltd, London 1970). In general *A. convoluta* resembles the bryozoan *Bugula neritina L.* and both occur together in certain areas of the Northeastern Gulf of Mexico.

ISOLATION AND PURIFICATION OF BRYOSTATINS

A variety of methods can be used to isolate and purify the bryostatins from samples of *B. neritina* and *A. convoluta*, including solvent extraction, partition chromatography, silica gel chromatography, liquid-liquid distribution in a Craig apparatus, absorption on resins, and crystalization from solvents. These procedures are also described in copending application Ser. No. 513,148, filed July 12, 1983, which is expressly incoporated by reference herein.

All solvents employed for chromatography were redistilled. Column chromatography was performed using either Sephedex LH-20, from Pharmacia Fine Chemicals AB, Uppsala, Sweden, or silica gel (70-230mesh) from E. Merck, Darmstadt. HPLC columns (9.4×500 nm) employed were the Partisil-10 M-9-ODS-2 (c-18 reversed phase) and Partisil-10 M-9 columns from Whatman, Inc., Clifton, N.J. An Altex HPLC with System Controller Model 420 and Model 110A pumps effected the final separations. Preparative and Reversed Phase (KC-18) LTC plates were provided by Whatman, Silica gel GF Uniplates were supplied by Analtech, Inc., Newark, Del. Plates were visualized by UV light and/or detected by anisaldehydeacetic acid-sulfuric acid spray (plates heated to about 150° for 5 to 10 minutes). Fractions were collected with either Gilson FC-80 (microfractionator) or FC-220 (rack-track fractionator) equipment and a Gilson UV monitor Model HM was used for chromatographic fractionations. Melting points are uncorrected and were observed with a Kofler-type melting point apparatus. Ultraviolet spectra were recorded with a Hewlett-Packard 8450A UV/VIS spectrometer. Optical rotations were recorded using a Perkin-Elmer Model 214 polarimetr. Mass spectra were recorded with a MAT-312 mass spectrometer and infrared spectra with a Nicolet FTIR Model MX-1 spectrometer. The NMR spectra were obtained with Bruker WH-90, WH-400, and the Varian XL-100 instruments. Deuteriochloroform was employed as solvent with tetramethylsilane as internal standard.

Five hundred kg wet weight of the *B. neritina* were immersed in 2- propanol immediately after collecting and were shipped to the processing site in that condition. The shipping solution (150 gallons) was drained from the animals and concenrated to an aqueous slurry using a Buchi R-150 E. evaporator at 50° C. This concentrate was divided into portions and repeatedly extracted with methylene chloride (5 to 6 times). The combined, dried methylene chloride extracts from the shipping solution weighed 511.0 g and was toxic to mice at an injected dose of 3.75 mg/kg.

After draining off the shipping solution, the marine animals were chopped up and further extracted with a mixture of methylene chloride and methanol (1:1) for two weeks at ambient temperature. The resulting solution was drained from the animals and one part of water to four parts of solution was added to produce phase separation. The lower phase (mostly methylene choride) was removed and evaporated to dryness using reduced pressure at 40°–45° C. To the remaining upper phase was added sufficient methylene chloride and methanol to produce a single phase (a ratio of 4:2:1 of upper phase:methylene chloride:methanol, respectively) and this solution was returned to the animal material for a second extraction at ambient temperature for 12 days. The solution resulting from the 2nd extraction was drained from the animals and water was again added to produce phase separation. The lower phase was separated and evaporated to dryness. A total of 366.1 g of dried methylene chloride extract was obtained from the two methylene chloride-methanol extractions of the animals The dried methylene chloride extracts (derived from the shipping solution and from extraction of the chopped animals) were further separated by taking small portions and subjecting each to solvent partitioning beginning with methanol:water (9:1)/hexane (4 times). The dried hexane extracts were inactive in P 388 mouse tumor tests. The aqueous mthanol layers were further diluted with water to a ratio of 8:2 and were extracted repeatedly with carbon tetrachloride (9 times). The carbon tetrachloride extracts were dried and assayed for antitumor activity. The 149.6 g portion derived from the shipping solution was toxic to mice at a dose of 1.5 mg/kg while the 64.3 g amount derived from the methylene chloride-methanol extraction of the chopped animals was active in a PS mouse tumor test system, producing a 46% increase in lifespan at a dose of 10 mg/kg.

The entire extraction and solvent partitioning process described above is shown in schematic form in Chart A.

A similar procedure was used for *A. convoluta*. Thus, 245 kg. of *A. convoluta* wet weight, were initially reduced to a 61 g carbon tetrachloride PS active fraction as outlined in Chart B, Part 1. The gel permeation-partition type chromatographic separation employing Sephadex HL-20 with 2:3 methylene chloride-methanol as solvent caused a further rapid concentration in fraction D of the major antineoplastic constituents. A useful further separation and concentration was achieved by repeating this step as shown in Part 2 of Chart B. Fraction H seemed to contain the most potent antineoplastic constituents and was further separated by careful fractionation on silica gel to yield active fraction M. The silica gel chromatographic separation with changes in solvent was further expanded to produce active fraction N. The relatively small weight of N (37.5 ng) allowed partial separation by preparative layer chromatography to yield active fraction 0. Even the 18.2 mg fraction 0 from some 245 kg of animal was still a challenging mixture that required extensive reverse phase and normal phase HPLC procedures for final separation. By this means bryostatins 4 (1a) and 6 (1b) were isolated in 1.6 mg and 0.6 mg yields respectively.

Meanwhile the promising Sephadex LH-20 fractions G and I were combined as outlined in Chart B Part 3 and subjected to the same type of fractionation as just summarized for obtaining bryostatins 4 and 6. However, the active fraction P corresponding to fraction M of the preceding separation was considerably more complicated and required the introduction of a very careful partition chromatographic step utilizing the LH-20 gel. The resulting PS in vivo very active fraction Q was separable into the principal active antineoplastic constituent of *A. convoluta* utilizing the techniques developed for separating fractions M-O. Additional quantities of bryostatins 4 (1a, 6.0 mg) and 6 (1b, 5.7 mg) were isolated accompanied by bryostatin 5 (1c, 3.1 mg) and a new bryostatin designated 8 (2, 4.2 mg). The combined total yields of bryostatins 4 and 6 amounted to $3.1 \times 10^{-6}\%$ and $2.6 \times 10^{-6}\%$, bryostatin 5, $1.3 \times 10^{-6}\%$ and bryostatin 8, $1.7 \times 10^{-6}\%$. Results of present PS in vivo antineoplastic evaluations (cf. Separation Scheme Part 3) of bryostatin 4–6 suggests that bryostatin 8 will eventually be found to exhibit similar remarkably high levels.

A parallel study of *Bugula neritina* antineoplastic components also led to the assignment of the structures indicated here for bryostatins 4 and 6. Recognition of bryostatin 8 as a member of this unique series of macrocyclic lactones first arose from viewing the characteristic reddish-purple color produced upon heating a thin-layer chromatogram of the substance sprayed with anisaldehyde reagent. Detailed interpretation of the 400 MHz $^1$H-NMR (Table 1) and $^{13}$C-NMR (Table 2) indicated that bryostatin 8 retained the basic bryopyran ring system and substitution pattern of bryostatin 1. The principal differences seemed to be at C-7 and C-20 where the acetate and (E,E)-octa-2,4-dienoate esters appeared to be absent. Application of the solution phase secondary ion mass spectrometric techniques to bryostatin 8 that we developed for routine detection of molecular ions proved rewarding. A solfolane solution containing sodium iodide gave a molecular ion complex at 903 $[M+Na]^+$ and an important fragment ion at 815 $[M+Na-88]^+$. Elimination of only 88 mass units led to the assumption that bryostatin 8 was esterified at C-7 and C-20 with butyrate substituents.

As part of the structural elucidation of bryostatin 2 it was found that bryostatin 1 could be selectively hydrolyzed using 1% hydrochloric acid in aqueous-methanol. The reaction led to bryostatin 2 as major product and suggested that the steric hindrance around C-20 was responsible for this very helpful selectivity. When bryostatin 8 was allowed to react with 1% hydrochloric acid in aqueous methanol for 1 day at room temperature the major product was presumed to be C-20 butyrate ester if accompanied by the isomeric 1g on the basis of mass spectral and proton magnetic resonance studies. A solution phase secondary ion spectrum of the hydrolysis product exhibited a molecular ion complex at 833 $[M+Na]^+$ and a quite revealing fragment ion at 745 $[M+Na-88]^+$. Thus loss of one butyl ester by selective hydrolysis and the second by mass spectral promoted cleavage provided compelling support for the C-7, C-20 dibutyrate structure 2 for bryostatin 8. Non-branching of the butyl group was ascertained by the NMR studies of bryostatins 4, 6 and 8.

When structures for the principal antineoplastic constituents of *A. convoluta* were established a possible relationship between this animal and the related *Bugula neritina* came under scrutiny. Voucher animal specimens for all prior collections along with 100 plus kilogram amounts of *A. convoluta* available from the 1981 and more recent (1982) recollections were closely examined. Amounts ranging from <0.2% to approximately 3% dry weight of *Bugula neritina* were found growing from the *A. convoluta* in a parasitic or epiphytic-like manner. The 1981 recollection described herein was found to have approximately 2.5% by weight of attached *Bugula neritina*. From our experience with the isolation and characterization of bryostatins 4-6 from *B. neritina* collected in the same general area as *A. convoluta*, the yields of these bryostatins seem to be two to four times greater than would be expected from *A. convoluta* containing some 2.5% of *B. neritina*. But this proportion was too close to safely conclude that they were produced by *A. convoluta*. On the other hand bryostatin 8 was isolated from *A. convoluta* in a quantity 50 times greater than would be expected from the companion *B. neritina*. Thus, bryostatin 8 seems to be a genuine constituent of *A. convoluta* and/or both animals have a relationship where the bryostatins may be transferred and concentrated by the *A. convoluta*. Alternatively, if the real source of the bryostatins resides in a common food source such as a dinoflagellate these relationships may be even more complex.

The isolation and purification methods chosen can be monitored at each step by performing in vitro and/or in vivo antitumor tests as described by R. I. Geran, N. H. Greenberg, M. M. MacDonald, A. M. Schumacher and B. S. Abbot in *Cancer Chemother. Rep.* Part 3, Vol. 3 (2): 1–103 (1972); and by Schmidt, J. M.; Pettit, G. R. in *Experimentia*, 34: 659–660 (1978). Such tests include the determination of the concentration of active material rquired to inhibit the growth of tumor cells in culture, (e.g., the concentration required to inhibit growth by 50 percent or the $ED_{50}$) and of the dose of active material required to prolong the life of mice bearing transplanted tumors.

Thus, Bryostatin 4 has been shown to inhibit the PS cell line with an $ED_{50}$ of $10^{-3}$ to $10^{-4}$ μg/kg and produces a 62% increase in life extension at 46 μg/kg. Similarly, Bryostatin 8 has an $ED_{50}$ of $1.3 \times 10^{-3}$ in the murine $P_{388}$ lymphocytic leukemia assay (PS cell line). The other Bryostatins claimed herein also were shown to be effective antineoplastic agents, with Bryostatin 5 having an $ED_{50}$ in the PS cell line of $1.3 \times 10^{-3}$ to $2.6 \times 10^{-4}$ μg/ml and, an in vivo life extension of 88% at 185 μg/kg; Bryostatin 6 having an $ED_{50}$ of $3.0 \times 10^{-3}$ μg/ml and an in vivo life extension of 82% at 185 μg/kg; and Bryostatin 7 having an $ED_{50}$ in the PS cell line of $2.6 \times 10^{-5}$ μg/ml, and an in vivo life extension of 77% at 92 μg/kg.

The dosage administered will be dependent upon the identity of the neoplastic diease, the type of host involved, its age, health, weight, kind of concurrent treatment, if any, frequency of treatment and therapeutic ratio.

Illustratively, dosage levels of the administered active ingredients can be: intravenous, 0.1 to about 200 mg/kg; intraperitoneal, 1 to about 500 mg/kg; subcutaneous, 1 to about 500 mg/kg; intramuscular, 1 to about 500 mg/kg; orally, 5 to about 1000 mg/kg; intranasal instillation, 5 to about 1000 mg/kg; and aerosol, 5 to about 1000 mg/kg of animal (body) weight.

Expressed in terms of concentration, an active ingredient can be present in the compositions of the present invention for localized use about the cutis, intranasally, pharyngolaryneally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triclyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a steric salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

For use as aerosols the active ingredients can be packaged in a presurized aerosol container together with a gaseous or liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral or anti-neoplastic agents can be easily prepared in unit dosage form with the employment of pharmaceutical materials which themselves are available in the art and can be prepared by established procedures.

The administration of bryostatins is useful for treating animals or humans bearing a neoplastic disease, for example, acute myelocytic leukemia, acute lymphocytic leukemia, malignant melanoma, adenocarcinoma of lung, neuroblastoma, small cell carcinoma of lung, breast carcinoma, colon carcinoma, ovarian carcinoma, bladder carcinoma, and the like.

DESCRIPTION OF THE PREFERRED EMBODIMENTS

The present invention is seen more fully by the Examples given below.

EXAMPLE 1

Isolation and Purification of Bryostatin 4

The methylene chloride phase of a methylene chloride-methanol-water extract of *Bugula neritina* (109 kg wet wt., Gulf of Mexico) was successively partitioned in 9:1 to 4:1 methanol-water between hexane and carbon tetrachloride. The overall separations were guided by bioassay (PS system) and the carbon tetrachloride fraction was subjected to an extensive series of gel permeation (Sephadex LH-20, 2:3 methylene chloride-methanol), silica gel (methylene chloride-methanol) partition (Sephadex LH-20, hexane-methylene chloride-methanol 10:10:1), Prep TL (hexane-ethyl acetate), reverse phase (C-18, methanol-water) and normal phase (partisil 10, ethyl acetate-heptane-methanol-water) HPL chromatographic procedures. Recrystallization from methylene chloride-methanol afforded 44.5 mg ($4.1 \times 10^{-5}$ yield) of bryostatin 4 as an amorphous powder melting at 198°–200° C.; FAB[4] MS m/z 894 (M+ for $C_{46}H_{70}O_{17}$); $[\alpha]^{27}D + 93.6°$; (c=0.032, $CH_3OH$); UV ($CH^3OH$) $\lambda_{max}$ ($\epsilon$, 36,500); IR (KBr) 3470, 2980–2945, 1740, 1725, 1660–1645, 1440, 1390, 1370, 1290, 1240, 1170, 1100, 1080, 1050, and 1000 cm$^{-1}$; and $^{13}C$ NMR as entered (tentative assignments) on Formula I-4.

Detailed interpretation of the 400 MHz NMR spectrum of bryostatin 4 uncovered a series of signals that very closely corresponded to the high resolution proton assignments for the bryopyran ring system of bryostatins 13[a] and 2.3[b]. In addition, the side-chain protons of the esters at C-7 and C-20 characteristic of bryostatins 1–3 were absent. However, the $^{13}C$ NMR signals at δ 172.03 and δ 172.22 suggested the presence of new ester substitution at C-7 and C-20. Such a conclusion was further strengthened by the C-7 carbon resonance at δ 72.46 and the C-20 carbon resonance at δ 79.13. Similarly, in the $^1H$-NMR spectrum of bryostatin 1, the C-7 proton appeared at δ 5.10 (m) and the C-20 proton at δ 5.167 as a sharp singlet. Both signals were very characteristic of the bryostatin 1 molecular geometry.

Because of substantial difficulties in recognizing the molecular ion in mass spectra of bryostatins, by a variety of methods, a new series of techniques based on solution phase secondary ion mass spectrometry was developed. These new procedures utilizing an alkali metal iodide, silver tetrafluoroborate or thallium tetrafluoroborate in sulfolane provided, with a great variety of substances including the bryostatins, the facile and routine detection of molecular ions. Application of these new mass spectral methods to further determining the structure of bryostatin 4 proved decisive. With sodium iodide in sulfolane, bryostatin 4 exhibited m/z 917 [M+Na]+ with the parent peak at 899 [M+Na-18]+, 829 [M+Na-88]+ and 815 [M+Na-102]+. With silver tetrafluoroborate was found m/z 1001 and 1003 [M+Ag$^{107}$ and Ag$^{109}$]+, 983 and 985 [M+Ag-18]+, 913 and 915 [M+Ag-88]+ and 899 and 901 [M+Ag-102]+. The loss of 88 mass units suggested elimination of a butyrate ester and water while the loss of 102 indicated elimination of a valerate group and water. Confirmation for these assumptions was obtained by assignment of the remaining $^1$H- and $^{13}$C-NMR signals. By this means the butyrate group was found to be normal and the valerate ester to be iso.

A study of the selective acid-catalyzed hydrolysis of bryostatin 1 (1a) to bryostatin 2 (1b) with hydrochloric acid was used as the basis for assigning positions to the butyrate and isovalerate esters. The relative steric compression of C-20 compared to C-7 seemed to favor hydrolysis at the less hindered position (C-7) and bryostatin 1 was found convertable to bryostatin 2 in reasonable yield 3b. Selective hydrolysis of bryostatin 4 (1 mg) with hydrochloric acid (1% in aqueous methanol, 24 hour at room temperature) yielded bryostatin 4a (0.72 mg, FAB MS m/z 833 [M+Na]+ for $C_{41}H_{62}O_{16}$) and as a minor product (100 μg) bryostatin 4b (FAB MS m/z 847 [M+Na]+ for $C_{42}H_{64}O_{16}$). From these results the butyrate ester was assigned to C-20 and the isovalerate ester to C-7.

EXAMPLE 2

Bryostatins 4, 5, 6, and 7 and Acylated Derivatives

Collection and Extraction: The recollection of *Bugula neritina* from the Eastern Gulf of Mexico (Alligator Harbor, Franklin County, Fla. in July 1982, afforded 50 kg wet weight of marine animal which was preserved in 2-propanol.

The extraction and solvent partitioning sequences described above provided 37.6 g of bryostatin-enriched methylene chloride extract (PS ED$_{50}$, 0.058 μg/ml). The extract was subjected to a series of column chromatographic separations which gave bryostatin 4 and later, bryostatins 5-7.

Bryostatin 5

From a succession of silica gel column chromatographies and gel permeation (Sephadex LH-20) chromatography, an active fraction (0.38 g) was isolated as a white amorphous powder with PS ED$_{50}$=1.6×10$^{-3}$ μg/ml and which contained bryostatins 4–7 by TLC (7:3 n-hexane:acetone and 2:3 n-hexane:ethyl acetate). By using dry column (2×60 cm) silica gel chromatographic methods with n-hexane:acetone (5:1→1:1) and n-hexane:ethyl acetate (2:1→1:2), six fractions were selected for further purification. The first fraction contained bryostatin 4. The second, third and fifth fractions were subjected to HPLC using Partisil-10M-9-ODS-2 (C-18 reversed phase) with a 1:1→9:1 methanol:water gradient (flow rate of 2 ml/min). The second fraction (15 mg) yielded pure bryostatin 5 (14.1 mg), melting at 169°–172° C. (needles from CH$_2$Cl$_2$—CH$_3$OH); FAB MS m/z 866 for $C_{44}H_{66}O_{17}$:[α]$^{27}$D+106.92 (c=0.028, CH$_3$OH); uv (CH$_3$OH) λ$_{max}$ 226 nm (ε 36,300); and ir (KBr) 3465, 2980–2935, 1740, 1725, 1660–1640, 1440, 1385, 1370, 1290, 1230, 1165, 1100, 1080, 1060, and 1000 cm$^{-1}$.

Bryostatin 6

The third fraction (65 mg) was subjected to the same HPLC final purification to yield bryostatin 6, 61.9 mg, mp 172°–175° C. (needles from CH$_2$Cl$_2$—CH$_3$OH); FAB MS m/Z 824 for $C_{41}H_{60}O_{17}$:[α]$^{27}$D+39.92 (c=0.05, CH$_3$OH); uv (CH$_3$OH) λ$_{max}$ 228 nm (ε 35,350); ir (KBr) 3460, 2980–2950, 1740, 1720, 1660–1650, 1440, 1380, 1370, 1280, 1240, 1160, 1100, 1080, 1060, and 100 cm$^{-1}$.

Acid-Catalyzed Hydrolysis of Bryostatin 5

A specimen of bryostatin 5 (3b, 1 mg) was subjected to hydrolysis in 0.5 ml of 1% hydrochloric acid for 24 hour at room temperature. The product, obtained by extraction with methylene chloride, washing with water and drying, was separated by HPLC reversed phase (C-18) column chromatography with methanol:water (from 1:1 to 9:1) to give the C-20 acetate 3e (300 μg) and the C-7 isovalerate 3f (100 μg).

The C-20 acetate was obtained as an amorphous powder from aqueous methanol melting at 153°–156° C.; FAB MS:m/z 805 [M+Na]+ for $C_{39}H_{58}O_{16}$, 787 [M+Na-18]+; ir (KBr):3475, 2980-2950, 1740, 1720, 1660–1638, 1435, 1380–1370, 1290, 1240, 1160, 1100, 1090, 1075, 1048, 1005 and 870 cm$^{-1}$.

The C-7 iso-valerate was obtained as amorphous solid from aqueous methanol melting at 147°–152° C.; FAB MS:mz 847 [M+Na]+ for $C_{42}H_{64}O_{16}$, 829 [M+Na-18]+ and 745 [M+Na-102°]+; ir (KBr):3470, 3435, 2975–2950, 1738, 1720, 1660–1635, 1440, 1390–1370, 1290, 1240, 1160, 1100, 1075, 1050, 1000, and 970 cm$^{-1}$.

The product was found to be the same as the compound from bryostatin 4 by similar acid hydrolysis.

Acid-Catalyzed Hydrolysis of Bryostatin 6

A specimen of bryostatin 6 (1 mg) was hydrolyzed using the same method as described for bryostatin 5. HPLC of the crude product in the same manner as described above provided the C-20 acetate (350 g), identical to that obtained from bryostatin 5, and the C-7 butyrate (150 μg).

The C-7 butyrate was obtained as an amorphous solid melting at 166°–170° C.; FAB MS:m/z 833 [M+Na]+ for $C_{41}H_{62}O_{16}$, 815 [M+Na-18]+ and 745 [M+Na-88]+; IR (KBr): 3475, 3430, 2975–2945, 1736, 1720, 1640, 1620, 1440, 1390, 1095, 1080, 1040, and 870 cm$^{-1}$.

Acid-Catalyzed Hydrolysis of Bryostatin 7

A sample of bryostatin 7 (1 mg) was hydrolyzed and the crude product purified by HPLC as outlined for bryostatin 5. The major product was the 20-acetate (370 μg) which was found to be the same product obtained from bryostatin 5.

Acetylation of Bryostatin 4

A sample of bryostatin 4 (9.0 mg) was treated with acetic anhydride (0.14 ml) and pyridine (0.2 ml) at room temperature for 4 hours. The mixture was poured into ice-water and extracted with methylene chloride. The extract was washed with dil, hydrochloride acid and water, concentrated and dried under reduced pressure. The crude product (9.5 mg) was purified by HPLC using the same procedure as described for bryostatin 5 above. Pure bryostatin 4 acetate 3 h (8.0 mg, 88.9% yield) was obtained as colorless needles from CH$_2$Cl$_2$—CH$_3$OH and melted at 519°-162° C.: [α]$^{27}_D$+58.71 (c=0.034, CH$_3$OH); uv (CH$_3$OH); λ$_{max}$ 227 nm (ε 36,600); ir (KBr) 3460, 2985-2935, 1745, 1730, 1660-1640, 1440, 1380, 1370, 1290, 1240, 1165, 1100, 1050, and 1000 cm$^{-1}$.

Tables I-IV show the $^1$H NMR and $^{13}$C NMR of bryostatins 5-7.

EXAMPLE 3

Separation of the gel permeation fractions G and I was even more challenging. Both fractions were combined and the 27.56 g combined fraction (Chart B Part 3) was first separated as summarized for fractions H→M to yield PS active fraction P (979 mg). At this stage it was found best to utilize a parition chromatographic procedure employing Sephadex LH-20 and the solvent system n-hexane-methylene chloride-methanol (10:10:1). A 3 cm×120 cm sized column was used and 12 ml fractions totalling 240 ml were collected. The resulting most active fraction (Q, 266 mg) was further fractioned as noted above for fraction M→N. The remaining separation steps were accomplished by the same general procedures employed with fraction 0 (Chart B Part 2). In order of elution appearance from the HPLC silica gel, were obtained bryostatin 4 (6.0 mg), bryostatin 5 (3.1 mg), bryostatin 6 (5.7 mg) and bryostatin 8 (4.2 mg). Presumably these substances are derived from the association of *Amathia convoluta* with *Bugula neritina*. However, bryostatin 8 appears to be a genuine constituent of *Amathia convoluta* and is characterized as follows.

Bryostatin 8

Bryostatin 8 was brought to analytical purity by rechromatography of the original 4.2 mg on a HPLC reverse phase C-18 column with methanol-water (from 50:50 to 90:10) as eluent. The resulting 2.8 mg of bryostatin 8 was obtained as a colorless amorphous powder melting at 170°-173° C: [α]$^{272}$D+49.9 (c, 0.04, CH$_3$OH); uv λ$^{CH3OH}$max 266 (ε 37,500); ir ν$^{KBr}_{max}$ 3551, 3475, 3415, 2975-2950, 1742, 1721, 1640, 1616, 1449, 1380, 1245, 1225, 1165, 1095, 1075, 1050 and 870 cm$^{-1}$; MS: 903 [M+Na]+. The 400 MHz proton, carbon-13 and carbon magnetic resonance data has been displayed in Tables V and VI in comparison with bryostatin 1.

Acid-Catalyzed Hydrolysis of Bryostatin 8 to Mono-Butyrate Esters

An 0.8 mg specimen of bryostatin 8 was hydrolyzed (24 hours at room temperature) in 0.2 ml of 1% hydrochloric acid in methanol. The products (0.5 mg) were isolated by HPLC reverse phase column (C-18) chromatography with methanol-water (from 50:50 to 90:10). Results of the solution phase secondary ion mass and high resolution $^1$H-NMR (400 MHz) spectral studies of the hydrolysis product have been recorded in the discussion section.

EXAMPLE 4

Derivatives of the Bryostatins

The bryostatins have free hydoxyl and replaceable acyl groups. Thus, various acyl esters of these compounds can be prepared by methods well known to those skilled in the art. Acyl derivatives of the bryostations include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like, (b) saturated or unsaturated, alicyclic carboxylic acids, for example, cyclobutanecarboxylic acid, cyclopentanecarboxylic acid, cyclopentenecarboxylic acid, methylcyclopentanecarboxylic acid, cyclohexanecarboxylic acid, dimethylcyclohexanecarboxylic acid, dipropylcyclohexanecarboxylic acid, and the like;

(c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like;

(d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano- and lower alkoxyhydrocarbon carboxylic acids include hydrocarboncarboxylic acids as given above which are substituted by one or more of halogen, nitro, hydroxy, keto, amino, cyano, or thiocyano, or loweralkoxy, advantageously lower alkoxy of not more than six carbon atoms, for example, methoxy, ethoxy, propoxy, butoxy, amyloxy, hexyloxy, and isomeric forms thereof. Examples of substituted hydrocarbon carboxylic acids are:

mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4′-dichlorobenzilic acid;
o-, m-, and p-nitrobenzoic acid;

cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
malic acid;
citric acid;
isocitric acid;
6-methylsalicylic acid;
mandelic acid;
levulinic acid;
pyruvic acid;
glycine;
alamine;
valine;
isoleucine;
leucine;
phenylalanine;
proline;
serine;
threonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;

and the like.

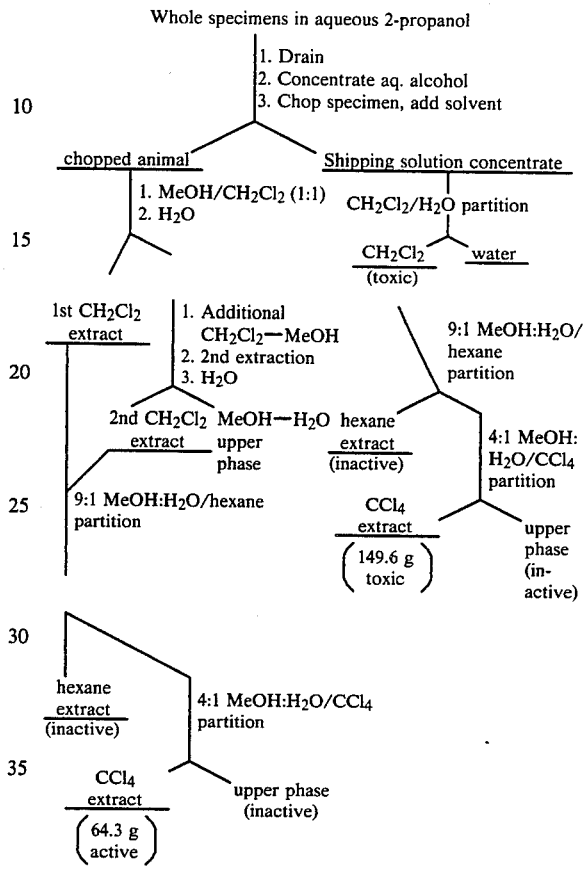

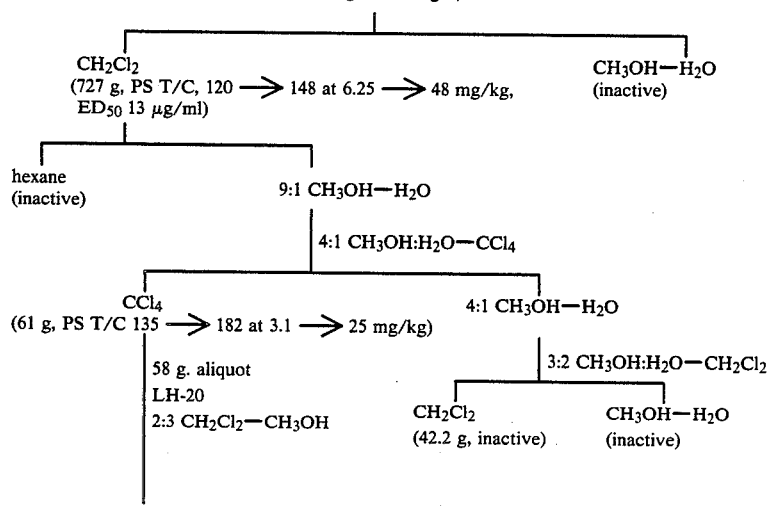

CHART B
| | A | B | C | D | E | F |
|---|---|---|---|---|---|---|
| PS ED$_{50}$ | $4.2 \times 10^{-2}$ | 16 | 9.8 | (38.9 g) | 9 | 16 |
| T/C (mg) | inactive | inactive | 126(12) | 131 ⟶ 168 (3 ⟶ 12) | inactive | inactive |
Separation Scheme Part 2
Combined Fraction D
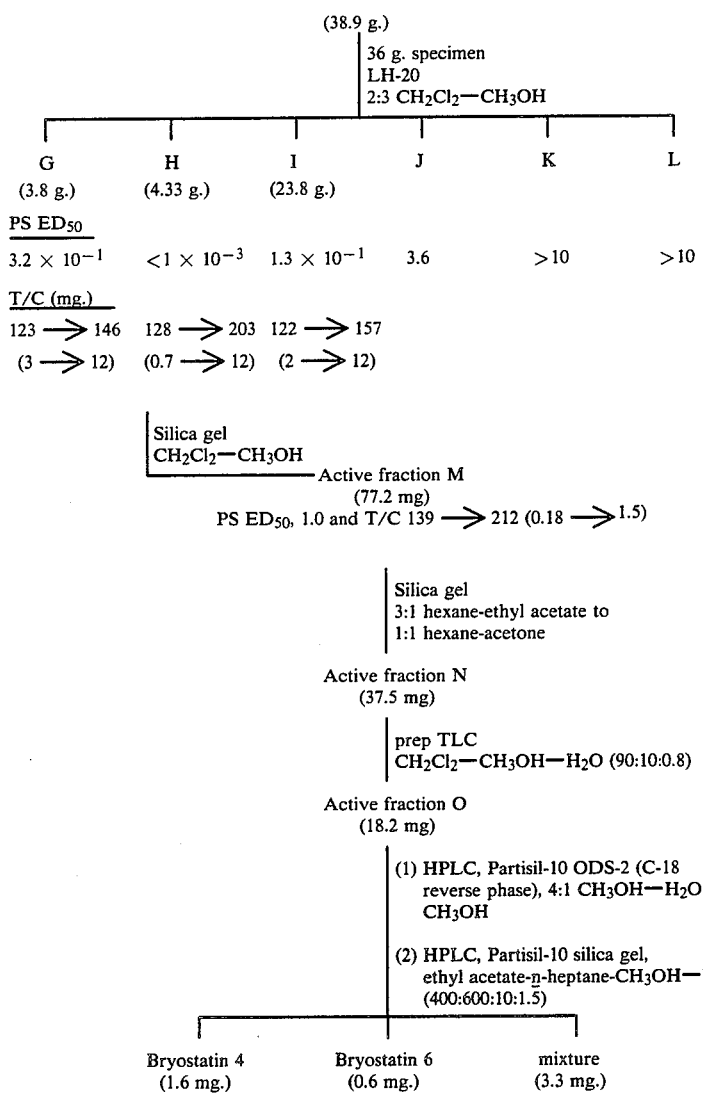
Separation Scheme Part 3
Combined Fraction G and I

CHART B (27.56 g.)
│ Silica gel
│ $CH_2Cl_2$—$CH_3OH$

Active fraction P
(979 mg.)
PS ED$_{50}$, $6.6 \times 10^{-2}$, T/C 190 → 192 (3 → 12)
│ LH-20
│ n-hexane-$CH_2Cl_2$—$CH_3OH$ (10:10:1)

Active fraction Q
PS ED$_{50}$, $4.5 \times 10^{-2}$, T/C 165 → 192 (0.37 → 1.5)
│ silica gel
│ 3:1 n-hexane-ethyl acetate to
│ 1:1 n-hexane acetone Active fraction R
(110 mg.)
│ prep TLC
│ $CH_2Cl_2$—$CH_3OH$—$H_2O$ (90:10:0.8)

Active fraction S
(51.2 mg.)

(1) HPLC, Partisil-10 ODS-2 (C-18 reverse phase) 4:1 $CH_3OH$—$H_2O$ to $CH_3OH$ (2) HPLC, Partisil-10 silica gel, ethyl acetate-n-heptane-$CH_3OH$—$H_2O$ (400:600:10:1.5)

| Bryostatin 4 (6.0 mg.) | Bryostatin 5 (3.1 mg.) | Bryostatin 6 (5.7 mg.) | Bryostatin 8 (4.2 mg.) | mixture (5.5 mg.) |
|---|---|---|---|---|
| PS ED$_{50}$ | | | | |
| $3.1 \times 10^{-3}$ → | $1.2 \times 10^{-4}$ → | $1.0 \times 10^{-5}$ | $3.6 \times 10^{-3}$ | $1.3 \times 10^{-3}$ |
| $6.7 \times 10^{-4}$ | $2.6 \times 10^{-4}$ | | | |
| T/C (mg.) | | | | |
| 162 → 162 | 145 → 188 | 139 → 182 | | 132 → 178 |
| (0.046 → 0.0925) | (0.046 → 0.185) | (0.046 → 0.185) | | (3 → 12) |

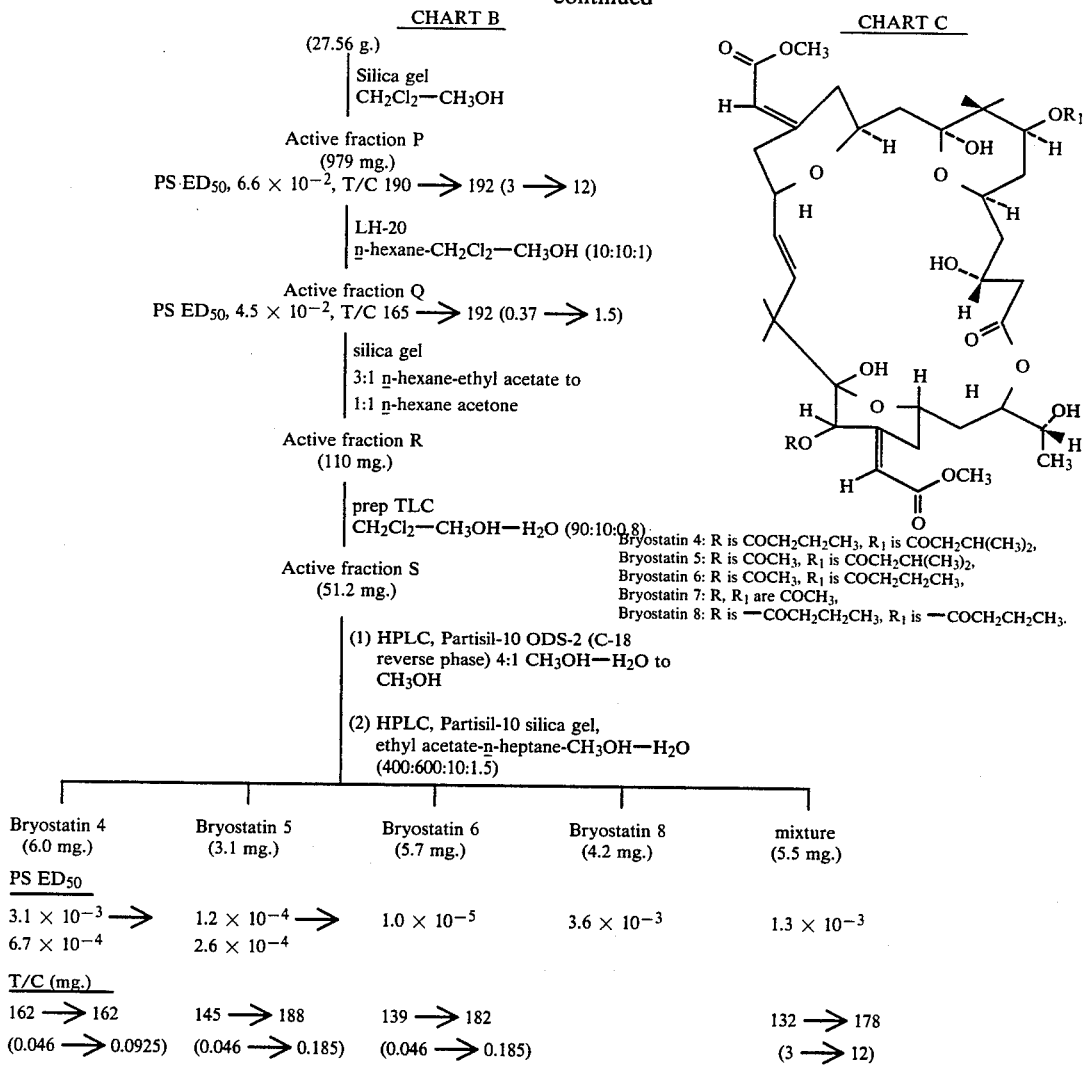

CHART C

Bryostatin 4: R is $COCH_2CH_2CH_3$, R$_1$ is $COCH_2CH(CH_3)_2$,
Bryostatin 5: R is $COCH_3$, R$_1$ is $COCH_2CH(CH_3)_2$,
Bryostatin 6: R is $COCH_3$, R$_1$ is $COCH_2CH_2CH_3$,
Bryostatin 7: R, R$_1$ are $COCH_3$,
Bryostatin 8: R is —$COCH_2CH_2CH_3$, R$_1$ is —$COCH_2CH_2CH_3$.

FORMULAS

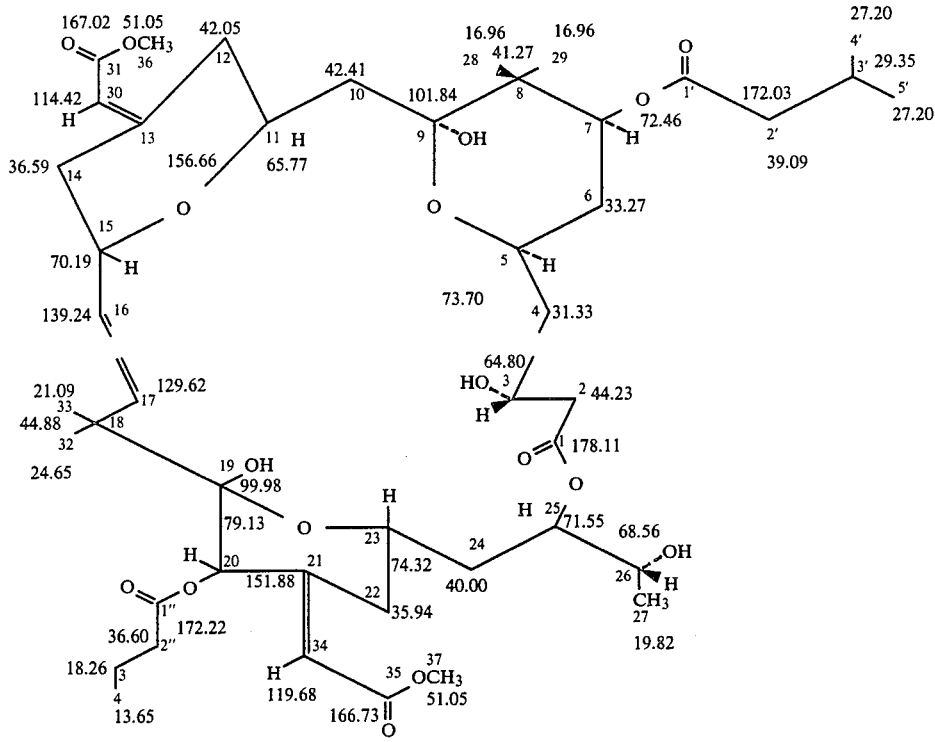

Bryostatin 4 (with $^{13}$C—NMR)
Formula I-4

TABLE I

| | $^1$H NMR (1) | | | |
|---|---|---|---|---|
| | Bryostation 7 | | Bryostatin 1 | |
| Position | δ (ppm) | Multiplicity (J Hz) | δ (ppm) | Multiplicity (J Hz) |
| 2 | 1.413, 2.512 | m,m | 2.45 | m |
| 3 | 4.14 | m | 4.19 | m |
| 4 | 1.62, 2.00 | m,m | 1.55, 1.95 | m,m |
| 5 | 4.21 | m | 4.1 | m |
| 6 | 1.45, 1.67 | m,m | 1.4, 1.5 | m,m |
| 7 | 5.139 | m | 5.15 | m |
| 10 | 1.50, 1.99 | m,m | 2.1~2.2 | m |
| 11 | 3.95 | m | ~3.95 | m |
| 12 | 2.175 | m | 2.1~2.2 | m |
| 14 | 1.83, 2.05 | m,m | 1.9,~2.0 | m,m |
| 15 | 4.06 | m | 4.08 | m |
| 16 | 5.300 | dd(8.44, 15.76) | 5.300 | dd(8.3, 15.9) |
| 17 | 5.747 | d(15.76) | 5.758 | d(15.9) |
| 20 | 5.081 | s | 5.162 | s |
| 22 | 1.80, 2.05 | m,m | ~1.90 | m |
| 23 | 3.625 | m | ~3.65 | m |
| 24 | 1.90, 2.00 | m,m | 1.95 | m |
| 25 | 5.17 | m | 5.19 | m |
| 26 | 3,60 | m | 3.73 | m |
| 27 | 1.215 | d(6.45) | 1.226 | d(6.3) |
| 28* | 1.134 | s | 1.132 | s |
| 29* | 0.979 | s | 0.982 | s |
| 30 | 5.657 | s | 5.657 | s |
| 32* | 0.979 | s | 0.982 | s |
| 33* | 0.917 | s | 0.919 | s |
| 34 | 5.951 | s | 5.983 | s |
| 36 | 3.685 | s | 3.68 | s |
| 37 | 3.658 | s | 3.65 | s |
| R$_1$ = 2' | 2.058 | s | 2.051 | s |
| R = 2" | 2.042 | s | 5.796 | d(15.3) |
| R = 3" | | | 7.261 | m |
| R = 4" | | | 6.157 | m |
| R = 5" | | | 6.157 | m |
| R = 6" | | | ~2.15 | m |
| R = 7" | | | 1.42 | m |

TABLE I-continued

| | $^1$H NMR (1) | | | |
|---|---|---|---|---|
| | Bryostation 7 | | Bryostatin 1 | |
| Position | δ (ppm) | Multiplicity (J Hz) | δ (ppm) | Multiplicity (J Hz) |
| R = 8" | | | 0.904 | t(7.3) |

*Assignment for these four group may be interchanged.

TABLE II

| | $^{13}$C NMR | |
|---|---|---|
| | Bryostation 7 | Bryostatin 1 |
| Position | δ (ppm) | δ (ppm) |
| 1 | 172.22 | 172.29 |
| 2 | 44.23 | 44.29 |
| 3 | 64.76 | 71.62 |
| 4 | 31.20 | 31.42 |
| 5 | 73.70 | 73.73 |
| 6 | 33.40 | 35.09 |
| 7 | 72.95 | 73.11 |
| 8 | 41.04 | 41.11 |
| 9 | 101.87 | 101.94 |
| 10 | 42.34 | 36.04 |
| 11 | 65.71 | 68.50 |
| 12 | 42.02 | 36.56 |
| 13 | 156.82 | 157.18 |
| 14 | 36.43 | 40.00 |
| 15 | 70.25 | 70.22 |
| 16 | 139.11 | 139.24 |
| 17 | 129.66 | 129.66 |
| 18 | 44.84 | 44.94 |
| 19 | 98.88 | 99.11 |
| 20 | 79.13 | 79.13 |
| 21 | 151.72 | 152.08 |
| 22 | 36.00 | 42.31 |
| 23 | 74.45 | 64.83 |
| 24 | 39.94 | 42.02 |
| 25 | 71.59 | 74.19 |
| 26 | 68.50 | 65.71 |
| 27 | 19.85 | 21.90 |

TABLE II-continued

$^{13}$C NMR

| Position | | Bryostation 7 δ (ppm) | Bryostatin 1 δ (ppm) |
|---|---|---|---|
| | 28 | } 16.86 | } 16.90 |
| | 29 | | |
| | 30 | 114.29 | 114.15 |
| | 31 | 166.96 | 167.06 |
| | 32 | { 24.60 or 21.12 | { 21.15 or 19.79 |
| | 33 | 21.12 or 24.60 | 19.79 or 21.15 |
| | 34 | 119.74 | 119.65 |
| | 35 | 166.73 | 166.80 |
| | 36 | } 51.05 | } 51.05 |
| | 37 | | |
| R$_1$ | 1' | 171.08 | 171.15 |
| R$_1$ | 2' | 21.48 | 33.43 |
| R | 1" | 169.30 | 165.63 |
| R | 2" | 21.12 | 118.74 |
| R | 3" | | 146.39 |
| R | 4" | | 128.49 |
| R | 5" | | 145.42 |
| R | 6" | | 35.09 |
| R | 7" | | 24.66 |
| R | 8" | | 13.68 |

TABLE III

$^1$H NMR

| | Bryostation 5 (K217) | | Bryostatin 6 (K218) | | Bryostatin 4 (K550) | |
|---|---|---|---|---|---|---|
| Position | δ (ppm) | Multiplicity (J Hz) | δ (ppm) | Multiplicity (J Hz) | δ (ppm) | Multiplicity (J Hz) |
| 2 | 2.46 | m | 2.42 | m | 2.45 | m |
| 3 | 4.12 | m | 4.17 | m | 4.16 | m |
| 4 | 1.56, 203 | m,m | 1.53, 1.99 | m,m | 1.61, 2.04 | m,m |
| 5 | 4.21 | m | 4.21 | m | 4.22 | m |
| 6 | 1.20, 1.70 | m,m | 1.43, 1.71 | m,m | 1.40, 1.72 | m,m |
| 7 | 5.087 | m | 5.14 | m | 5.10 | m |
| 10 | 1.70, 2.08 | m,m | 1.79, 2.02 | m,m | 1.65, 2.15 | m,m |
| 11 | 3.88 | m | 3.95 | m | 3.87 | m |
| 12 | 2.15~2.18 | m | 2.17 | m | 2.18 | m |
| 14 | 1.85, 20.5 | m,m | 1.94, 2.05 | m,m | 1.85, 2.05 | m,m |
| 15 | 4.06 | m | 4.07 | m | 4.08 | m |
| 16 | 5.299 | dd(2.4, 15.8) | 5.292 | dd(8.34, 15.72) | 5.250 | dd(8.4, 15.7) |
| 17 | 5.751 | d(15.8) | 5.737 | d(15.72) | 5.738 | d(15.7) |
| 20 | 5.165 | s | 5.074 | s | 5.167 | s |
| 22 | 1.89, 2.03 | m,m | 1.85, 2.03 | m,m | 1.85, 2.00 | m,m |
| 23 | 3.98 | m | 3.96 | m | 3.98 | m |
| 24 | 1.83, 1.97 | m,m | 1.84, 1.94 | m,m | 1.78, 1.90 | m,m |
| 25 | 5.11 | m | 5.074 | m | 5.07 | m |
| 26 | 3.75 | m | 3.716 | m | 3.77 | m |
| 27 | 1.204 | d(6.46) | 1.205 | d(7.21) | 1.211 | d(6.3) |
| 28* | 1.135 | s | 1.126 | s | 1.138 | s |
| 29* | 0.994 | s | 0.973 | s | 0.996 | s |
| 30 | 5.656 | s | 5.647 | s | 5.660 | s |
| 32* | 0.985 | s | 0.973 | s | 0.985 | s |
| 33* | 0.918 | s | 0.904 | s | 0.920 | s |
| 34 | 5.958 | s | 5.942 | s | 5.961 | s |
| 36 | 3.683 | s | 3.676 | s | 3.686 | s |
| 37 | 3.657 | s | 3.650 | s | 3.658 | s |
| 2' | 2.46 | m | 2.26 | m | 2.25 | m |
| 3' | 1.8~1.9 | m | 1.60 | m | 1.88~1.99 | m |
| 4' 5' | } 1.16 | d(14.5) | 0.90 | t(7.2) | 1.16 | d(14.5) |
| 2" | 2.057 | s | 2.051 | s | 2.25 | m |
| 3" | | | | | 1.60 | m |
| 4" | | | | | 0.901 | t(7.2) |

*Assignments for these four groups may be interchanged.

TABLE IV

$^{13}$C NMR

| Position | Bryostatin 5 δ (ppm) | Bryostatin 6 δ (ppm) | Bryostatin 4 δ (ppm) |
|---|---|---|---|
| 1 | 178.04 | 173.52 | 178.11 |
| 2 | 44.19 | 44.26 | 44.23 |
| 3 | 64.76 | 64.80 | 64.80 |
| 4 | 31.26 | 31.26 | 31.33 |
| 5 | 73.73 | 73.76 | 73.70 |
| 6 | 33.27 | 33.47 | 33.27 |
| 7 | 72.37 | 72.66 | 72.46 |
| 8 | 41.27 | 41.11 | 41.27 |
| 9 | 101.87 | 101.90 | 101.84 |
| 10 | 42.41 | 42.34 | 42.41 |
| 11 | 65.84 | 65.74 | 65.77 |
| 12 | 42.05 | 42.05 | 42.05 |
| 13 | 156.46 | 156.85 | 156.66 |
| 14 | 36.40 | 39.59 | 36.59 |
| 15 | 70.22 | 70.22 | 70.19 |
| 16 | 139.24 | 139.11 | 139.24 |
| 17 | 129.62 | 129.72 | 129.62 |
| 18 | 44.88 | 44.88 | 44.88 |
| 19 | 98.95 | 98.91 | 98.98 |
| 20 | 79.16 | 79.13 | 79.13 |
| 21 | 151.75 | 151.88 | 151.88 |
| 22 | 35.87 | 35.94 | 35.94 |
| 23 | 74.48 | 74.48 | 74.32 |
| 24 | 40.00 | 40.00 | 40.00 |
| 25 | 71.55 | 71.59 | 71.55 |
| 26 | 68.56 | 68.56 | 68.56 |
| 27 | 19.85 | 19.82 | 19.82 |
| 28 29 | } 16.93 | 16.96 | 16.96 |
| 30 | 114.55 | 114.32 | 114.42 |
| 31 | 167.02 | 167.02 | 167.02 |
| 32 | { 24.63 or 21.06 | 24.63 or 21.12 | 24.65 or 21.09 |
| 33 | 21.06 or | 21.12 or | 21.09 or |

TABLE IV-continued

13C NMR

| Position | Bryostatin 5 δ (ppm) | Bryostatin 6 δ (ppm) | Bryostatin 4 δ (ppm) |
|---|---|---|---|
|  | 24.63 | 24.63 | 24.65 |
| 34 | 119.78 | 119.78 | 119.68 |
| 35 | 166.73 | 166.76 | 166.73 |
| 36 | 51.05 | 51.08 | 51.05 |
| 37 |  |  |  |
| 1' | 172.19 | 172.29 | 172.03 |
| 2' | 39.06 | 39.50 | 39.09 |
| 3' | 29.31 | 18.59 | 29.35 |
| 4' | 27.17 | 13.68 | 27.20 |
| 5' |  |  |  |
| 1" | 169.30 | 169.33 | 172.22 |
| 2" | 21.45 | 21.48 | 36.60 |
| 3" |  |  | 18.26 |
| 4" |  |  | 13.65 |

TABLE V

1H NMR
(400 MHz, Deuteriochloroform Solution)

| | Bryostatin 8 | | Bryostatin 1 | |
|---|---|---|---|---|
| Position | δ (ppm) | Multiplicity (J Hz) | δ (ppm) | Multiplicity (J Hz) |
| 2 | 2.450 | m | 2.45 | m |
| 3 | 4.166 | m | 4.19 | m |
| 4 | 1.64, 2.01 | m,m | 1.55, 1.95 | m,m |
| 5 | 4.202 | m | 4.1 | m |
| 6 | 1.46, 1.76 | m,m | 1.4, 1.5 | m,m |
| 7 | 5.164 | m | 5.15 | m |
| 10 | 1.70, 2.06 | m,m | 2.1~2.2 | m |
| 11 | 3.820 | m | ~3.95 | m |
| 12 | 2.10~2.19 | m | 2.1-2.2 | m |
| 14 | 1.83, 2.03 | m,m | 1.9-2.0 | m,m |
| 15 | 4.04 | m | 4.08 | m |
| 16 | 5.295 | dd(8.45, 15.75) | 5.300 | dd(8.3, 15.9) |
| 17 | 5.758 | d(15.75) | 5.758 | d(15.9) |
| 20 | 5.103 | s | 5.162 | s |
| 22 | 1.89, 2.02 | m,m | ~1.90 | m |
| 23 | 3.982 | m | ~3/65 | m |
| 24 | 1.89, 1.97 | m,m | 1.95 | m |
| 25 | 5.170 | m | 5.19 | m |
| 26 | 3.767 | m | 3.73 | m |
| 27 | 1.214 | d(6.50) | 1.226 | d(6.3) |
| 28[a] | 1.135 | s | 1.132 | s |
| 29[a] | 0.983 | s | 0.982 | s |
| 30 | 5.663 | s | 5.657 | s |
| 32[a] | 0.983 | s | 0.982 | s |
| 33[a] | 0.922 | s | 0.919 | s |
| 34 | 5.961 | s | 5.983 | s |
| 36 | 3.685 | s | 3.68 | s |
| 37 | 3.655 | s | 3.65 | s |
| 2' | 2.27 | m | 2.051 | s |
| 3' | 1.66 | m |  |  |
| 4' | 0.923 | t(7.2) |  |  |
| 2" | 2.27 |  | 5.796 | d(15.3) |
| 3" | 1.66 |  | 7.261 | m |
| 4" | 0.917 | t(7.2) | 6.157 | m |
| 5" |  |  | 6.157 | m |
| 6" |  |  | ~2.15 | m |
| 7" |  |  | 1.42 | m |
| 8" |  |  | 0.904 | t(7.3) |

[a]Assignments for these four groups may be interchanged

TABLE VI

13C-NMR
(Deuteriochloroform Solution)[a]

| Position | Bryostatin 8 δ (ppm) | Bryostatin 1 δ (ppm) |
|---|---|---|
| 1 | 173.26 | 172.29 |
| 2 | 44.26 | 44.29 |
| 3 | 64.86 | 71.62 |
| 4 | 31.29 | 31.42 |
| 5 | 73.76 | 73.73 |
| 6 | 33.47 | 35.09 |
| 7 | 72.46 | 73.11 |
| 8 | 41.14 | 41.11 |
| 9 | 101.94 | 101.94 |
| 10 | 42.50 | 36.04 |
| 11 | 65.93 | 68.50 |
| 12 | 42.18 | 36.56 |
| 13 | 156.30 | 157.18 |
| 14 | 36.62 | 40.00 |
| 15 | 70.22 | 70.22 |
| 16 | 139.37 | 139.24 |
| 17 | 129.59 | 129.66 |
| 18 | 44.94 | 44.94 |
| 19 | 99.04 | 99.11 |
| 20 | 79.26 | 79.13 |
| 21 | 151.85 | 152.08 |
| 22 | 36.04 | 42.31 |
| 23 | 74.35 | 64.83 |
| 24 | 40.00 | 42.02 |
| 25 | 71.62 | 74.19 |
| 26 | 68.56 | 65.71 |
| 27 | 19.85 | 21.90 |
| 28 | 16.93 | 16.90 |
| 29 |  |  |
| 30 | 114.64 | 114.15 |
| 31 | 167.02 | 167.06 |
| 32 | 24.63 or 21.12 | 21.15 or 19.79 |
| 33 | 21.12 or 24.63 | 19.79 or 21.15 |
| 34 | 119.71 | 119.65 |
| 35 | 166.70 | 166.80 |
| 36 | 51.02 | 51.05 |
| 37 |  |  |
| 1' | 172.09 | 171.15 |
| 2' | 36.59 | 33.43 |
| 3' | 18.59 |  |
| 4' | 13.68 |  |
| 1" | 171.96 | 165.63 |
| 2" | 36.59 | 118.74 |
| 3" | 18.29 | 146.39 |
| 4" | 13.68 | 128.49 |
| 5" |  | 145.42 |
| 6" |  | 35.09 |
| 7" |  | 24.66 |
| 8" |  | 13.68 |

We claim:
1. A compound of the Formula I:

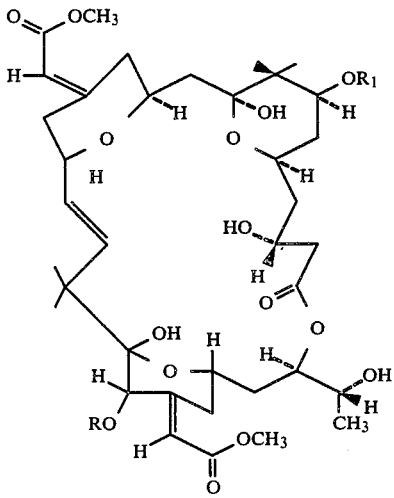

wherein R is
- (a) —COCH$_2$CH$_2$CH$_3$, or
- (b) —COCH$_3$; and wherein R$_1$ is
- (a) —COCH$_2$CH(CH$_3$)$_2$,
- (b) —COCH$_2$CH$_2$CH$_3$, or
- (c) —COCH$_3$.

2. Bryostatin 4, a compound of claim 1, wherein R is —COCH$_2$CH$_2$CH$_3$ and R$_1$ is —COCH$_2$CH(CH$_3$)$_2$.

3. Bryostatin 5, a compound of claim 1, wherein R is —COCH$_3$ and R$_1$ is —COCH$_2$CH(CH$_3$)$_2$.

4. Bryostatin 6, a compound of claim 1, wherein R is —COCH$_3$ and R$_1$ is COCH$_2$CH$_2$CH$_3$.

5. Bryostatin 7, a compound of claim 1, wherein R and R$_1$ are —COCH$_3$.

6. Bryostatin 8, a compound of claim 1, wherein R is —COCH$_2$CH$_2$CH$_3$ and R$_1$ is —COCH$_2$CH$_2$CH$_3$.

* * * * *